United States Patent
Park et al.

(10) Patent No.: US 11,064,908 B2
(45) Date of Patent: Jul. 20, 2021

(54) APPARATUS AND METHOD FOR OBTAINING ANTIOXIDANT INDEX

(71) Applicant: SAMSUNG ELECTRONICS CO., LTD., Suwon-si (KR)

(72) Inventors: Jin Young Park, Hwaseong-si (KR); Sung Mo Ahn, Yongin-si (KR); Min Jung Son, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 106 days.

(21) Appl. No.: 16/439,915

(22) Filed: Jun. 13, 2019

(65) Prior Publication Data

US 2019/0380622 A1    Dec. 19, 2019

(30) Foreign Application Priority Data

Jun. 19, 2018  (KR) .......................... 10-2018-0070491

(51) Int. Cl.
*G06T 7/00* (2017.01)
*A61B 5/103* (2006.01)
*A61B 5/00* (2006.01)
*G16H 30/40* (2018.01)

(52) U.S. Cl.
CPC .......... *A61B 5/1032* (2013.01); *A61B 5/0077* (2013.01); *A61B 5/441* (2013.01); *G06T 7/0012* (2013.01); *A61B 5/0013* (2013.01); *G06T 2207/30088* (2013.01); *G16H 30/40* (2018.01)

(58) Field of Classification Search
None
See application file for complete search history.

(56) References Cited

U.S. PATENT DOCUMENTS

| | | | |
|---|---|---|---|
| 8,231,914 B2 | 7/2012 | McAnalley et al. | |
| 9,096,882 B2 | 8/2015 | Meyer et al. | |
| 9,402,546 B2 | 8/2016 | Segman | |
| 10,215,757 B2 | 2/2019 | Kim et al. | |
| 2005/0171413 A1* | 8/2005 | Blair | A61B 5/14532 600/310 |
| 2010/0123802 A1* | 5/2010 | Kim | G06K 9/4652 348/234 |

(Continued)

FOREIGN PATENT DOCUMENTS

| | | |
|---|---|---|
| EP | 2 287 591 A2 | 2/2011 |
| EP | 3 175 783 A1 | 6/2017 |

(Continued)

OTHER PUBLICATIONS

Yoshioka et al., "Use of image analysis to estimate anthocyanin and UV-excited fluorescent phenolic compound levels in strawberry fruit", Breeding Science, 2013, pp. 211-217, 7 pages total.

*Primary Examiner* — Delomia L Gilliard
(74) *Attorney, Agent, or Firm* — Sughrue Mion, PLLC

(57) ABSTRACT

An apparatus for obtaining an antioxidant index may include an image acquirer configured to acquire an image by capturing a correction reference object and a skin of a user and a processor configured to determine a first degree of yellowness of the correction reference object and a second degree of yellowness of the skin based on the image, and determine an antioxidant index of the user based on the first degree of yellowness and the second degree of yellowness.

18 Claims, 7 Drawing Sheets

(56) References Cited

U.S. PATENT DOCUMENTS

| | | | |
|---|---|---|---|
| 2010/0214421 A1* | 8/2010 | Qu | H04N 1/6033 |
| | | | 348/207.1 |
| 2010/0284610 A1* | 11/2010 | Yoshikawa | G06T 7/0012 |
| | | | 382/164 |
| 2015/0285787 A1 | 10/2015 | Msika et al. | |
| 2016/0334332 A1 | 11/2016 | Magnussen et al. | |
| 2017/0138793 A1* | 5/2017 | Qu | G01N 21/251 |
| 2017/0307624 A1 | 10/2017 | Kim et al. | |
| 2019/0110716 A1* | 4/2019 | Sunwoo | A61B 5/6898 |
| 2019/0125249 A1* | 5/2019 | Rattner | A61B 5/443 |

FOREIGN PATENT DOCUMENTS

| | | |
|---|---|---|
| JP | 2004-333151 A | 11/2004 |
| JP | 2006-337222 A | 12/2006 |
| KR | 10-1481172 B1 | 1/2015 |
| KR | 10-2017-0101837 A | 9/2017 |
| WO | 2009/046954 A2 | 4/2009 |

* cited by examiner

APPARATUS AND METHOD FOR OBTAINING ANTIOXIDANT INDEX

CROSS-REFERENCE TO RELATED APPLICATION(S)

This application claims priority from Korean Patent Application No. 10-2018-0070491, filed on Jun. 19, 2018, in the Korean Intellectual Property Office, the entire disclosure of which is incorporated herein by reference for all purposes.

BACKGROUND

1. Field

Apparatuses and methods consistent with example embodiments relate to an apparatus and method for non-invasively obtaining an antioxidant index.

2. Description of Related Art

Active oxygen is important as a biological protective factor for, for example, the bactericidal action of leukocytes, but excessive production of active oxygen in the body is known to cause various tissue diseases.

Common factors for generating active oxygen include stress, alcohol, peroxides, drugs, and the like, and the active oxygen generated by these factors may cause various diseases, such as cerebral diseases, cardiovascular diseases, cancer, digestive tract diseases, liver diseases, arteriosclerosis, aging, and the like.

The body has a series of oxidation protection systems to protect itself from oxygen toxicity. It is important to consume enough antioxidant ingredients to properly operate the oxidation protection systems. Antioxidants include vitamin E, vitamin C, carotenoids, and flavonoids. For antioxidant activity, it is desirable to consume foods containing the antioxidants as much as possible, and hence there is a need for technology that can easily identify the amount of antioxidants in the body.

SUMMARY

One or more example embodiments provide an apparatus and a method for obtaining antioxidant index in a non-invasive manner based on image processing. One or more example embodiments also provide an apparatus a method for obtaining antioxidant index in a non-invasive manner while miniaturization of the apparatus is possible.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The following description relates to an apparatus and method for non-invasively obtaining an antioxidant index on the basis of image processing.

According to an aspect of an example embodiment, there is provided an apparatus for obtaining an antioxidant index, including: an image acquirer configured to acquire an image in which a correction reference object and a skin of a user are captured; and a processor configured to determine a first degree of yellowness of the correction reference object and a second degree of yellowness of the skin based on the image, and configured to determine an antioxidant index of the user based on the first degree of yellowness and the second degree of yellowness.

The image acquirer may be configured to acquire the image by capturing the correction reference object and the skin by using a camera.

The processor may be configured to analyze the image based on an International Commission on Illumination (CIE) chromaticity analysis.

The processor may be configured to determine a b-value related to the first degree of yellowness and a b-value related to the second degree of yellowness.

The processor may be configured to obtain at least one of a difference between the first degree of yellowness and the second degree of yellowness or a ratio between the first degree of yellowness and the second degree of yellowness, and configured to determine the antioxidant index based on the at least one of the difference or the ratio and a predetermined antioxidant index estimation model.

The predetermined antioxidant index estimation model may define a relationship between the antioxidant index and the at least one of the difference or the ratio between the first degree of yellowness and the second degree of yellowness.

The processor may be configured to control to output information for guiding an action of the user prior to acquiring the image through a camera.

The apparatus may further include a noise remover configured to remove noise from the acquired image.

The image acquirer may be configured to acquire the image from an external device communicatively connected to the apparatus.

The correction reference object may include an object in yellow color.

According to an aspect of an example embodiment, there is provided a method of obtaining an antioxidant index, including: acquiring an image in which a correction reference object and a skin of a user are captured; determining a first degree of yellowness of the correction reference object and a second degree of yellowness of the skin based on the image; and determining an antioxidant index of the user based on the first degree of yellowness and the second degree of yellowness.

The acquiring may include acquiring the image by capturing the correction reference object and the skin using a camera.

The determining the first degree of yellowness and the second degree of yellowness may include analyzing the image based on an International Commission on Illumination (CIE) chromaticity analysis.

The determining the first degree of yellowness and the second degree of yellowness may further include determining a b-value related to the first degree of yellowness and a b-value related to the second degree of yellowness.

The determining the antioxidant index may include: obtaining at least one of a difference between the first degree of yellowness and the second degree of yellowness or a ratio between the first degree of yellowness and the second degree of yellowness; and determining the antioxidant index based on the at least one of the difference or the ratio and a predetermined antioxidant index estimation model.

The predetermined antioxidant index estimation model may define a relationship between the antioxidant index and the at least one of the difference or the ratio between the first degree of yellowness and the second degree of yellowness.

The method may further include controlling to output information for guiding an action of the user prior to acquiring the image through a camera.

The method may further include removing noise from the acquired image.

The acquiring may include acquiring the image from an external device.

The correction reference object may include an object in yellow color.

BRIEF DESCRIPTION OF THE DRAWINGS

These and/or other aspects will become apparent and more readily appreciated from the following description of the example embodiments, taken in conjunction with the accompanying drawing, in which.

DETAILED DESCRIPTION

Figure 1:
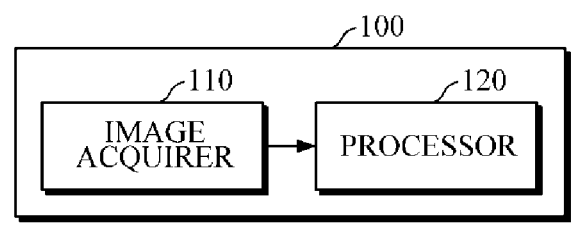
FIG. 1 is a diagram illustrating an apparatus for obtaining an antioxidant index according to an example embodiment.

Example embodiments are described in greater detail below with reference to the accompanying drawings. In the following description, like drawing reference numerals are used for like elements throughout the drawings. The relative size and depiction of these elements may be exaggerated for clarity, illustration, and convenience. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following example embodiments, when terms are specifically defined, the meanings of terms should be interpreted based on definitions, and otherwise, should be interpreted based on general meanings recognized by those skilled in the art.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and may be implemented by using hardware, software, or a combination of hardware and software.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a diagram illustrating an apparatus for obtaining an antioxidant index according to an example embodiment.

An apparatus 100 for obtaining an antioxidant index as shown in FIG. 1 is an apparatus capable of obtaining an antioxidant index of a user (or an object) through image processing and may be mounted in an electronic device. In addition, the apparatus 100 of FIG. 1 may be implemented as a separate apparatus from the electronic device and may be surrounded by a housing. In this case, the electronic device may include a mobile phone, a smartphone, a tablet computer, a notebook computer, a personal digital assistant (PDA), a portable multimedia player (PMP), a navigation system, an MP3 player, a digital camera, a wearable device, etc., and the wearable device may include wearable devices of various types, such as a wristwatch type, a wrist band type, a ring type, a belt type, a necklace type, an ankle band type, a thigh band type, a forearm band type, and the like. However, the electronic device and the wearable device are not limited to the aforementioned examples.

Referring to FIG. 1, the apparatus 100 may include an image acquirer 110 and a processor 120. The processor 120 may be configured with one or more processors and a memory, or a combination thereof.

The image acquirer 110 may acquire an image (hereinafter referred to as a "skin image") in which a correction reference object and a user's skin are captured. In this case, the correction reference object may be in yellow color to correct the influence of illumination change. For example, the correction reference object may include a yellow tape, yellow paper, a yellow sheet, and the like, but is not limited thereto. However, these are merely examples and the correction reference object is not limited thereto.

According to an example embodiment, the image acquirer 110 may include one or more cameras for capturing an image and may acquire the skin image by capturing both the correction reference object and the user's skin using the one or more cameras.

According to an example embodiment, the image acquirer 110 may acquire the skin image from an external device by communicating with the external device. For example, the image acquirer 110 may acquire the skin image from the external device using various communication technologies, such as Bluetooth communication, Bluetooth low energy (BLE) communication, near field communication (NFC), wireless local area network (WLAN) communication, Zig-Bee communication, Infrared data association (IrDA) communication, Wi-Fi direct (WFD) communication, ultra-wideband (UWB) communication, Ant+ communication, Wi-Fi communication, radio frequency identification (RFID) communication, 3$^{rd}$ generation (3G) communication, 4G communication, 5G communication, and the like. The external device may include a mobile phone, a smartphone, a tablet computer, a notebook computer, a PDA, a PMP, a navigation system, an MP3 player, a digital camera, a wearable device, and the like. However, the external device is not limited to the aforementioned examples and may include various devices that capture and/or store skin images.

The processor 120 may determine an antioxidant index of the user by analyzing the skin image. In this case, the antioxidant index may be an indicator of an amount of antioxidants (e.g., carotenoid and the like) that are accumulated in the body.

In the case of normal people, ingestion of antioxidants may cause carotenoderma, which increases the yellowness of the skin. Accordingly, the processor 120 may determine the antioxidant index by analyzing the degree of yellowness of the skin through the skin image.

The processor 120 may determine a degree of yellowness of the correction reference object and a degree of yellowness of the skin by analyzing the skin image. For example, the processor 120 may analyze the skin image using the International Commission on Illumination (CIE) chromaticity analysis (e.g., CIE L*a*b*) and determine a b-value of the correction reference object (hereinafter referred to as a "reference b-value"), which is related to a degree of yellowness of the correction reference object, and a b-value of the skin (hereinafter referred to as a "skin b-value"), which is related to a degree of yellowness of the skin.

A plurality of reference b-values and a plurality of skin b-values may be extracted depending on the size of the correction reference object in the skin image and the size of the skin in the skin image. In this case, the processor 120 may average the plurality of extracted reference b-values and the plurality of extracted skin b-values and determine the average values as the reference b-value and the skin b-value, respectively. However, the disclosure is not limited thereto. For example, the processor 120 may obtain values such as a total sum, a mean value, a median value, a maximum value, and a minimum value of the plurality of extracted reference b-values and the plurality of extracted skin b-values, respectively, or obtain a value calculated by applying a pre-defined function to the plurality of extracted reference b-values and the plurality of extracted skin b-values, respectively, and determine the obtained values as the reference b-value and the skin b-value, respectively.

The processor 120 may calculate a difference and/or a ratio of the degree of yellowness between the correction reference object and the skin and determine the user's antioxidant index using the calculated difference and/or ratio and an antioxidant index estimation model. Here, the antioxidant index estimation model, which defines the relationship between the antioxidant and the difference and/or ratio of the degree of yellowness between the correction reference object and the skin. The antioxidant index estimation model may be constructed in advance through regression analysis or machine learning and be stored inside or outside of the processor 120. The antioxidant index estimation model may be constructed in the form of a mathematical algorithm or a matching table, but is not limited thereto.

According to one embodiment, the processor 120 may generate an action guide information to guide a user's action to acquire the skim image through the camera and provide it to the user through an output means. In this case, the output means may include all or some of a visual output devices (e.g., a display and the like), an audio output devices (e.g., a speaker and the like), and a tactile output devices (e.g., a vibrator and the like).

In addition, the processor 120 may acquire the user's skin image by controlling the camera when a predetermined condition is satisfied.

According to an example embodiment, the apparatus 100 may determine the user's antioxidant index by analyzing the user's skin image and correct the influence of illumination change using the correction reference object so that it is possible to reduce the size of the apparatus (or miniaturize the apparatus) while maintaining the accuracy of the determination on the antioxidant index.

Figure 2:
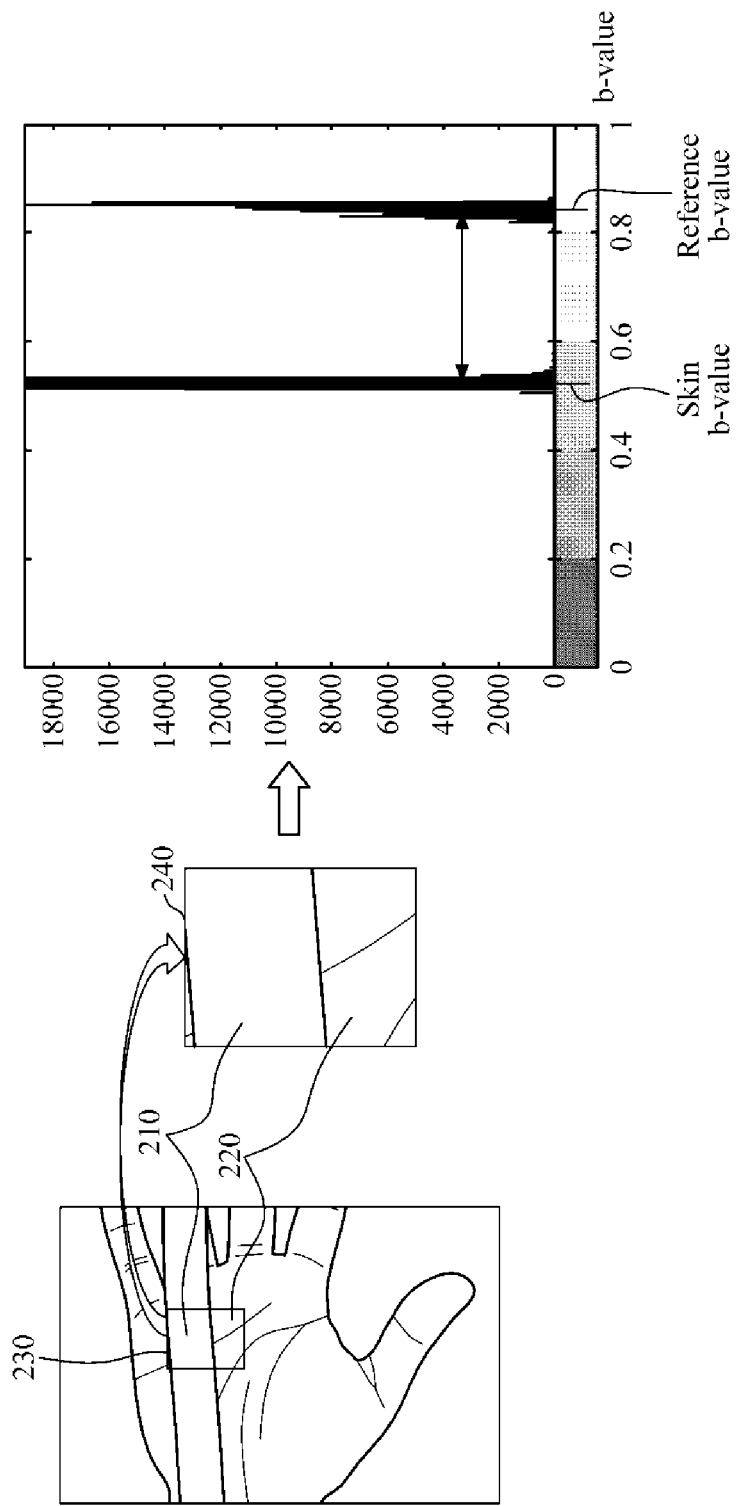
FIGS. 2 and 3 are diagrams for describing a process of obtaining an antioxidant index according to an example embodiment.
Figure 3:
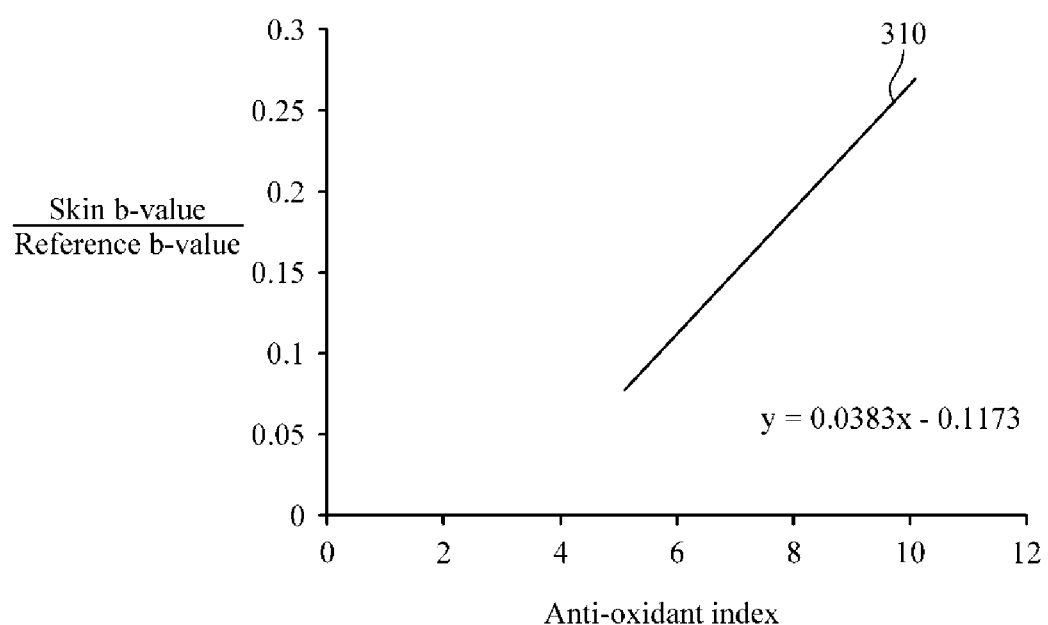

FIGS. 2 and 3 are diagrams for describing a process of obtaining an antioxidant index. In FIGS. 2 and 3, a yellow tape is used as a correction reference object.

Referring to FIGS. 1 to 3, the image acquirer 110 may acquire a skin image 240. A correction reference object 210 may be positioned on a region of a skin 220 of the user, and the skin image 240 may be an image obtained by capturing (e.g., photographing) the region including the correction reference object 210 and the skin 220 of the user. For example, the image acquirer 110 may acquire the image 240 from the external device, as described above with reference to FIG. 1. In another example, the image acquirer 110 may acquire the image 240 by capturing the region 230 using a camera.

The processor 120 may analyze the skin image 240 using the CIE chromaticity analysis (e.g., CIE L*a*b*) and determine a b-value (reference b-value) of the correction reference object 210 and a b-value (skin b-value) of the skin 220. In this case, as a result of the image analysis, when a plurality of b-values corresponding to the correction reference object 210 and a plurality of b-values corresponding to the skin 220 are extracted from the skin image 240, the processor 120 may determine an average of the reference b-values and an average of the skin b-values as the v-value of the correction reference object 210 and the b-value of the skin 220, respectively. However, the disclosure is not limited thereto.

The processor 120 may calculate a ratio of the skin b-value to the reference b-value (skin b-value/reference b-value) by dividing the skin b-value of the skin 220 by the reference b-value of the correction reference object 210 and determine the antioxidant index by applying the calculated ratio to a predetermined antioxidant index estimation model 310. The antioxidant index estimation model 310 may be a model that defines a relationship between the antioxidant index and the ratio between the reference b-value and the skin b-value.

In FIGS. 2 and 3, an example embodiment in which the antioxidant index is determined based on the ratio between the skin b-value and the reference b-value is described, but the disclosure is not limited thereto. For example, the processor 120 may calculate a difference between the reference b-value and the skin b-value and determine the antioxidant index based on the difference. The processor 120 may subtract the skin b-value from the reference b-value and determine the antioxidant index based on a result of subtraction. In this case, the processor 120 may use an antioxidant index estimation model that defines a relationship between the antioxidant index and a difference between the reference b-value and the skin b-value.

Figure 4:
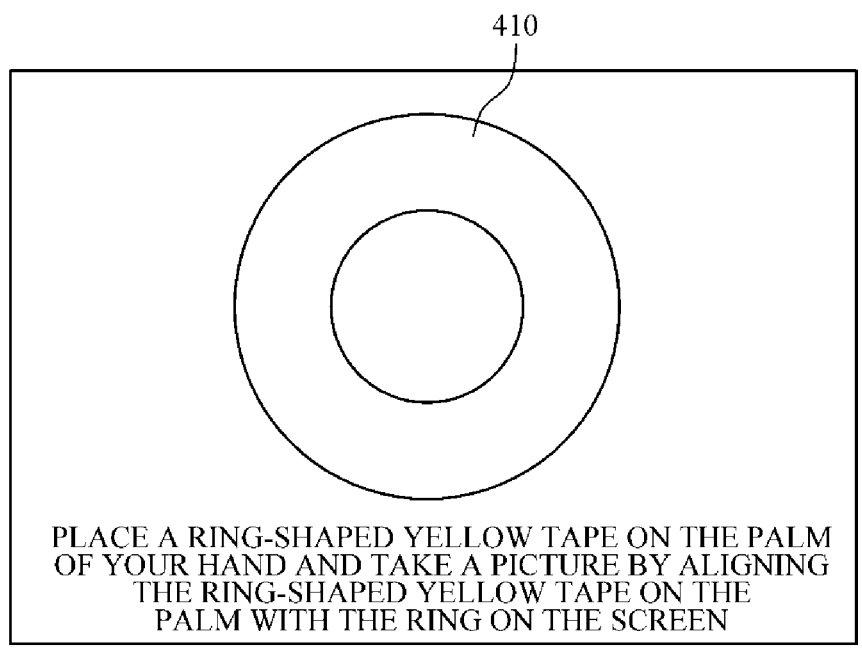
FIG. 4 is a diagram illustrating an example of output action guide information according to an example embodiment.

FIG. 4 is a diagram illustrating an example of output action guide information according to an example embodiment.

FIG. 4 illustrates an example embodiment of providing action guide information to guide a user to maintain a capturing area of a correction reference object and a capturing area of the skin to be constant, thereby improving reproducibility and accuracy in obtaining an antioxidant index.

Referring to FIG. 4, the apparatus 100 for obtaining an antioxidant index according to an example embodiment may display information (e.g., "Place a ring-shaped yellow tape on the palm of your hand and take a picture by aligning the ring-shaped yellow tape on the palm with the ring on the screen") for guiding a user's action to a display screen. In FIG. 4, the information is displayed on a lower portion of the display screen, but the position of the information is not limited thereto. In addition, the information may not be displayed according to an embodiment.

The apparatus 100 may display an indicator 410 that indicates a position of the correction reference object on the screen when the correction reference object and the skin are captured through a camera. In this case, the indicator 410 may be formed in the same shape as the shape of the correction reference object.

The apparatus 100 may acquire the skin image of the user by controlling the camera when a predetermined condition is satisfied. For example, the apparatus 100 may capture and obtain the skin image of the user by activating the camera when the correction reference object is placed at a position corresponding to the indicator 410.

In the example shown in FIG. 4, the ring-shaped correction reference object is used, but the disclosure is not limited thereto and the shape of the correction reference object may vary. For example, the correction reference object may be formed in various shapes, such as a star, a rectangle, a triangle, a circle, a rhombus, a pentagon, and the like, and in this case, the indicator 410 may also be altered according to the shape of the correction reference object.

Figure 5:
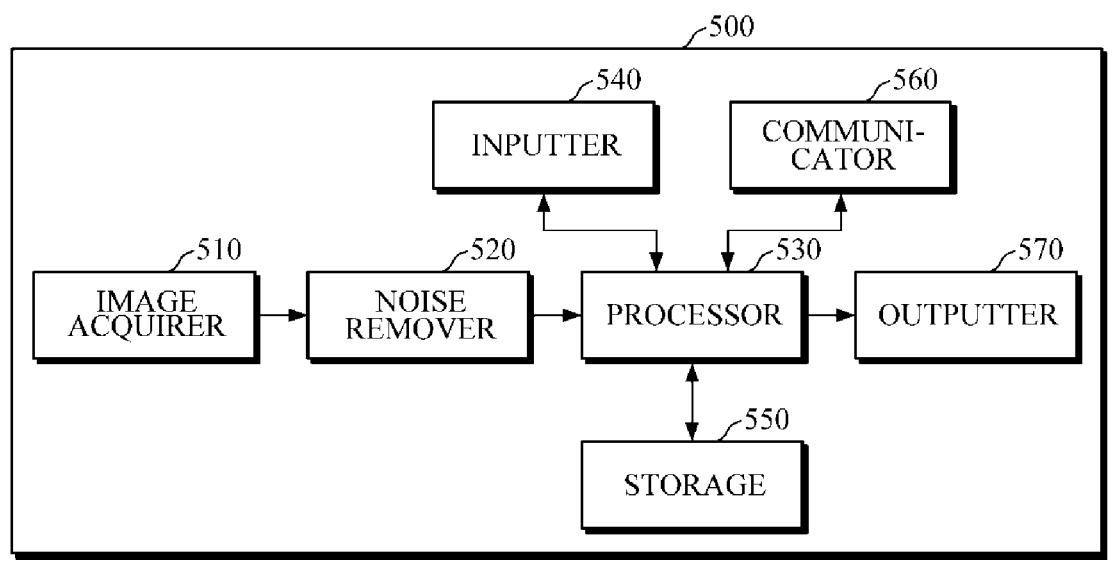
FIG. 5 is a diagram illustrating an apparatus for obtaining an antioxidant index according to an example embodiment.

FIG. 5 is a diagram illustrating an apparatus for obtaining an antioxidant index according to an example embodiment.

An apparatus 500 for obtaining an antioxidant index as shown in FIG. 5 is an apparatus capable of obtaining an antioxidant index of a user through image processing and may be mounted in an electronic device. In addition, the apparatus 500 of FIG. 5 may be formed as a separate apparatus from the electronic device and may be surrounded by a housing. The electronic device may include a mobile phone, a smartphone, a tablet computer, a notebook computer, a PDA, a PMP, a navigation system, an MP3 player, a digital camera, a wearable device, etc., and the wearable device may include wearable devices of various types, such as a wristwatch type, a wrist band type, a ring type, a belt type, a necklace type, an ankle band type, a thigh band type, a forearm band type, and the like. However, the electronic device and the wearable device are not limited to the aforementioned examples.

Referring to FIG. 5, the apparatus 500 may include an image acquirer 510, a noise remover 520, a processor 530, an inputter (or input interface) 540, a storage 550, a communicator 560, and an outputter (or an output interface) 570. Here, the image acquirer 510 and the processor 530 may be the same as the image acquirer 110 and the processor 120 of FIG. 1, respectively, and thus detailed descriptions thereof will not be reiterated.

The noise remover 520 may remove various noises from a skin image. To this end, the noise remover 520 may include various noise removal filters, such as an average filter, a Gaussian filter, a median filter, and the like.

The inputter 540 may receive various operation signals input by a user. According to an example embodiment, the inputter 540 may include a key pad, a dome switch, a touch pad (capacitive/resistive), a jog wheel, a jog switch, a hardware button, and the like. In particular, when a touch pad has a layered structure with a display, this structure may be referred to as a touch screen.

Programs or commands for an operation of the apparatus 500 may be stored in the storage 550 and data input and output to and from the apparatus 500 also may be stored. In addition, data processed by the apparatus 500 and data required for data processing of the apparatus 500 may be stored in the storage 550.

The storage 550 may include at least one type of storage medium, such as a flash memory, a hard disk type memory, a multimedia card micro type memory, a card-type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, and an optical disk. In addition, the apparatus 500 may operate an external storage medium, such as web storage providing a storage function of the storage 150.

The communicator 560 may communicate with the external device. For example, data processed by the apparatus 500 or processing result data of the apparatus 500 may be transmitted to the external device, or various types of data useful to estimate blood pressure may be received from the external device.

In this case, the external device may be medical equipment which uses the data input by the user, the data acquired or processed by the apparatus 500, and the information to be used for data processing of the apparatus 500, or may be a printer or display device to output a result. In addition, the external device may include, but not limited to, a digital TV, a desktop computer, a mobile phone, a smartphone, a tablet computer, a notebook computer, a PDA, a PMP, a navigation terminal, an MP3 player, a digital camera, a wearable device, and the like.

The communicator 560 may communicate with the external device using Bluetooth communication, BLE communication, NFC communication, WLAN communication, ZigBee communication, IrDA communication, WFD communication, UWB communication, Ant+ communication, Wi-Fi communication, RFID communication, 3G communication, 4G communication, 5G communication, and the like. However, these are examples and the communicator is not limited thereto.

The outputter 570 may output data processed by the apparatus 500 or processing result data of the apparatus 500. According to one embodiment, the outputter 570 may output the data dealt by the apparatus 500 or the processing result data of the apparatus 500 in at least one of audible, visual, and tactile methods. To this end, the outputter 570 may include a display, a speaker, a vibrator, etc.

Figure 6:
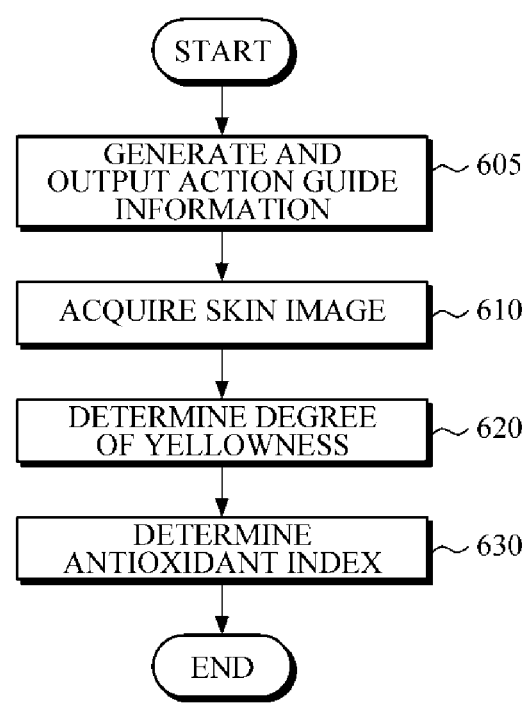
FIG. 6 is a flowchart illustrating a method of obtaining an antioxidant index according to an example embodiment.

FIG. 6 is a flowchart illustrating a method of obtaining an antioxidant index according to an example embodiment. The method of FIG. 6 may be performed by the apparatus 100 for obtaining an antioxidant index of FIG. 1.

Referring to FIGS. 1 and 6, the apparatus 100 for obtaining an antioxidant index may acquire a skin image of a user in 610. In this case, the skin image may be an image acquired by capturing both a correction reference object and the skin of the user.

According to an example embodiment, the apparatus 100 may include one or more cameras for capturing an image and may acquire the skin image by capturing both the correction reference object and the user's skin using the one or more cameras.

According to another example embodiment, the apparatus 100 may acquire the skin image from an external device by communicating with the external device which capture and/or store the skin image.

The apparatus 100 may determine a degree of yellowness of the correction reference object and a degree of yellowness of the skin by analyzing the skin image in 620. For example, the apparatus 100 may analyze the skin image using the CIE chromaticity analysis (e.g., CIE L*a*b*) and determine a reference b-value related to the degree of yellowness of the correction reference object and a skin b-value related to the degree of yellowness of the skin.

A plurality of reference b-values and a plurality of skin b-values may be extracted according to the size of the correction reference object in the skin image and the size of the ski in the skin image, and the apparatus 100 may average the plurality of extracted reference b-values and the plurality of extracted skin b-values, and determine the average values as the reference b-value and the skin b-value, respectively. However, the disclosure is not limited thereto. For example, the apparatus 100 may obtain values such as a total sum, a mean value, a median value, a maximum value, and a minimum value of the plurality of extracted reference b-values and the plurality of extracted skin b-values, respectively, or obtain a value calculated by applying a pre-defined function to the plurality of extracted reference b-values and the plurality of extracted skin b-values, respectively, and determine the obtained values as the reference b-value and the skin b-value, respectively.

The apparatus 100 may determine the antioxidant index of the user based on the degree of yellowness of the correction reference object and the degree of yellowness of the skin in 630. Here, the antioxidant index may be an indicator of an amount of antioxidants (e.g., carotenoid and the like) that are accumulated in the body.

For example, the apparatus 100 may calculate a difference or a ratio of the degree of yellowness between the correction reference object and the skin and determine the user's antioxidant index by using the calculated difference or ratio and an antioxidant index estimation model. Here, the antioxidant index estimation model, which defines the relationship between the antioxidant and the difference or ratio of the degree of yellowness between the correction reference object and the skin, may be constructed in advance through regression analysis or machine learning.

According to an example embodiment, the apparatus 100 may generate action guide information for guiding the user's action to acquire the skin image through the camera and provide the action guide information to the user through an output means according to the user's command, in 605.

Figure 7:
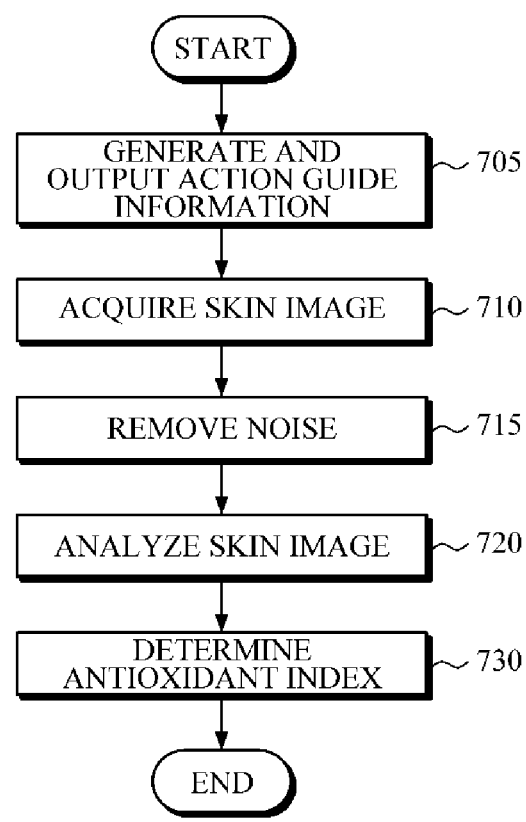
FIG. 7 is a flowchart illustrating a method of obtaining an antioxidant index according to an example embodiment.

FIG. 7 is a flowchart illustrating a method of obtaining an antioxidant index according to an example embodiment. The method of FIG. 7 may be performed by the apparatus 500 for obtaining an antioxidant index of FIG. 5. Here, operations 705, 710, 720, and 730 may be the same as operations 605, 610, 620, and 630, respectively, and thus detailed descriptions thereof will not be reiterated.

Referring to FIGS. 5 and 7, the apparatus 500 may acquire a skin image of a user and remove noise from the skin image, in 715. To this end, the apparatus 500 may include various noise removal filters, such as an average filter, a Gaussian filter, a median filter, and the like.

The example embodiments of the disclosure can be implemented as computer readable codes in a computer readable record medium. Codes and code segments constituting the computer program can be easily inferred by a skilled computer programmer in the art. The computer readable record medium includes any type of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

According to example embodiments, an antioxidant index may be obtained in a non-invasively manner based on image processing. Also, according to example embodiments, miniaturization of the apparatus becomes possible.

At least one of the components, elements, modules or units described herein may be embodied as various numbers of hardware, software and/or firmware structures that execute respective functions described above, according to an embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in some of block diagrams, communication between the components, elements or units may be performed through the bus. Functional aspects of the above embodiments may be implemented in algorithms that execute on one or more processors. Furthermore, the components, elements or units represented by a block or processing operations may employ any number of related art techniques for electronics configuration, signal processing and/or control, data processing and the like.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, various modifications and improvements made by those of ordinary skill in the art to concepts defined in the following claims should be understood to fall within the scope of the disclosure.

What is claimed is:

1. An apparatus for obtaining an antioxidant index, comprising:
an image acquirer configured to acquire an image in which a correction reference object and a skin of a user are captured; and
a processor configured to determine a first degree of yellowness of the correction reference object and a second degree of yellowness of the skin based on the image, and configured to determine an antioxidant index of the user based on the first degree of yellowness, the second degree of yellowness, and a predetermined antioxidant index estimation model, the predetermined antioxidant index estimation model defining a relationship between the antioxidant index and at least one of a difference between the first degree of yellowness and the second degree of yellowness or a ratio between the first degree of yellowness and the second degree of yellowness.

2. The apparatus of claim 1, wherein the image acquirer is configured to acquire the image by capturing the correction reference object and the skin by using a camera.

3. The apparatus of claim 1, wherein the processor is configured to analyze the image based on an International Commission on Illumination (CIE) chromaticity analysis.

4. The apparatus of claim 3, wherein the processor is configured to determine a b-value related to the first degree of yellowness and a b-value related to the second degree of yellowness.

5. The apparatus of claim 1, wherein the processor is configured to obtain at least one of the difference between the first degree of yellowness and the second degree of yellowness or the ratio between the first degree of yellowness and the second degree of yellowness, and configured to determine the antioxidant index based on the at least one of the difference or the ratio and the predetermined antioxidant index estimation model.

6. The apparatus of claim 1, wherein the processor is configured to control to output information for guiding an action of the user prior to acquiring the image through a camera.

7. The apparatus of claim 1, further comprising a noise remover configured to remove noise from the acquired image.

8. The apparatus of claim 1, wherein the image acquirer is configured to acquire the image from an external device communicatively connected to the apparatus.

9. The apparatus of claim 1, wherein the correction reference object comprises an object in yellow color.

10. A method of obtaining an antioxidant index, comprising:
acquiring an image in which a correction reference object and a skin of a user are captured;
determining a first degree of yellowness of the correction reference object and a second degree of yellowness of the skin based on the image; and
determining an antioxidant index of the user based on the first degree of yellowness, the second degree of yellowness, and a predetermined antioxidant index estimation model, the predetermined antioxidant index estimation model defining a relationship between the antioxidant index and at least one of a difference between the first degree of yellowness and the second degree of yellowness or a ratio between the first degree of yellowness and the second degree of yellowness.

11. The method of claim 10, wherein the acquiring comprises acquiring the image by capturing the correction reference object and the skin using a camera.

12. The method of claim 10, wherein the determining the first degree of yellowness and the second degree of yellowness comprises analyzing the image based on an International Commission on Illumination (CIE) chromaticity analysis.

13. The method of claim 12, wherein the determining the first degree of yellowness and the second degree of yellowness further comprises determining a b-value related to the first degree of yellowness and a b-value related to the second degree of yellowness.

14. The method of claim 10, wherein the determining the antioxidant index comprises:
obtaining at least one of the difference between the first degree of yellowness and the second degree of yellowness or the ratio between the first degree of yellowness and the second degree of yellowness; and
determining the antioxidant index based on the at least one of the difference or the ratio and the predetermined antioxidant index estimation model.

15. The method of claim 10, further comprising controlling to output information for guiding an action of the user prior to acquiring the image through a camera.

16. The method of claim 10, further comprising removing noise from the acquired image.

17. The method of claim 10, wherein the acquiring comprises acquiring the image from an external device.

18. The method of claim 10, wherein the correction reference object comprises an object in yellow color.

* * * * *